US00PP30960P2

(12) United States Plant Patent
Horvath

(10) Patent No.: US PP30,960 P2
(45) Date of Patent: Oct. 22, 2019

(54) ***GEUM* PLANT NAMED 'CHERRY BOMB'**

(50) Latin Name: ***Geum* hybrid**
Varietal Denomination: Cherry Bomb

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 15/732,633

(22) Filed: Dec. 7, 2017

(51) Int. Cl.
*A01H 5/02* (2018.01)
*A01H 6/74* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt

(57) ABSTRACT

A new, distinct *Geum* plant as illustrated and described, characterized by ruffled semi double to single pink flowers.

1 Drawing Sheet

Latin name: *Geum* hybrid.
Cultivar name: 'Cherry Bomb'.

BACKGROUND OF THE INVENTION

The present invention relates to a new and distinct hybrid of *Geum* plant named 'Cherry Bomb' characterized by ruffled semi double to single pink flowers. The new *Geum* was discovered and developed as a seedling as part of an ongoing breeding and selecting program in Hebron, Ill. in 2010. The plant was raised from seed on open pollinated plants. The parents of the new plant are unknown. The selection of the new plant was made in 2014 and was due to its' ruffled semi double to single pink flowers. The initial asexual propagation of the new *Geum* plant was by division and took place at a nursery in Hebron, Ill. since 2015. Continued asexual propagation by division since that time has shown that the unique features of the new *Geum* plant are stable and reproduced true to type in successive generations. No plants of the new *Geum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

In the following description, color references are made to The Royal Horticultural Society Colour Chart (2001). The new *Geum* plant named 'Cherry Bomb' characterized by semi double to single flowers of pink RHS 185 C and 185 D fading to 159 A at the tips of the petals have been observed to be unique and stable. The parent plants are no longer available for comparison.

Plants of the new *Geum* can be compared to *Geum* 'Mai Tai' U.S. Plant Pat. No. 22,433, patented. 1. The new plant flower color is pink RHS 185 C and 185 D fading to 159 A at the tips of the petals while *Geum* 'Mai Tai' has a flower colors of RHS 53 B fading to 48 C and finally to 36 B and 36 C.

Plants of the new *Geum* can also be compared to *Geum* 'Sangria' not patented. 1. The new plant flower color is pink RHS 185 C and 185 D fading to 159 A at the tips of the petals while *Geum* 'Sangria' has a flower color of RHS 45 B. 2. The new plant also has flowers that measure 4 cm wide while *Geum* 'Sangria' has flowers that measure 5-6 cm wide.

DESCRIPTION OF PHOTOGRAPHS

Figure 1:
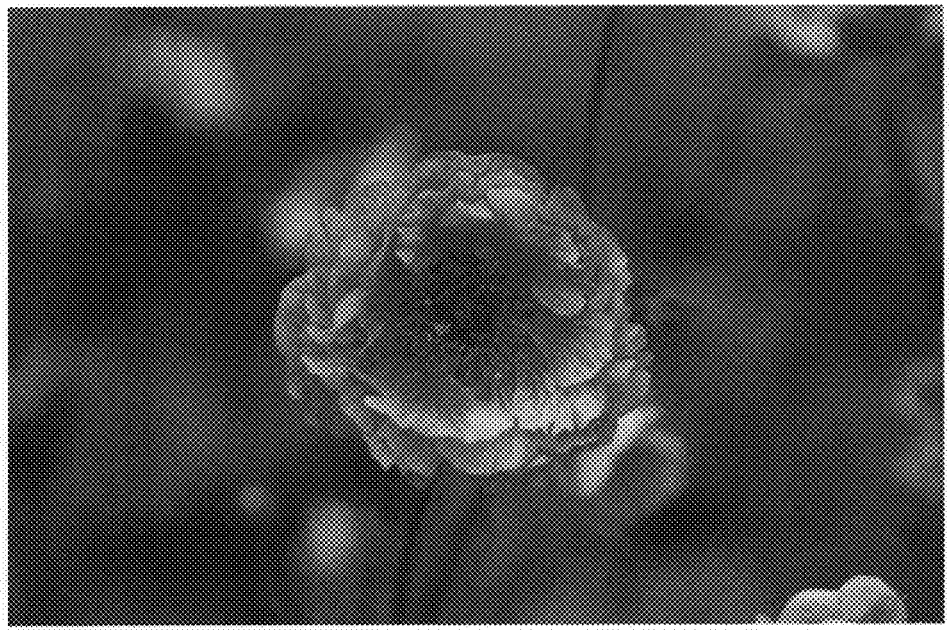
Figure 2:
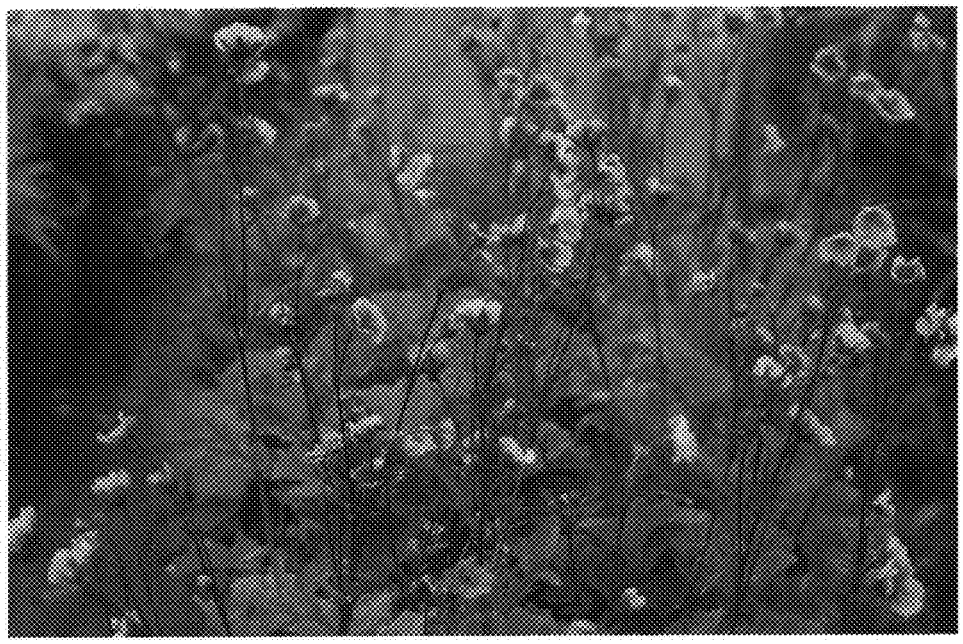

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a 1 gallon container for one year at a nursery in Hebron, Ill. Measurements and numerical values represent averages of typical plants.

Botanical classification: *Geum* hybrid cultivar 'Cherry Bomb'.

Parentage: Unknown.

Propagation: Vegetative division.

Plant description: Overall habit of the new *Geum* is basal clumps, with upright flower stems colored green at the base and red at the tips, topped by semi double to single flowers of pink RHS 185 C and 185 D fading to 159 A at the tips of the petals.

*Plant height.*—40 cm.

*Plant width.*—36 cm.

*Stem.*—Diameter: 3 mm.

*Stem or basal branches.*—Length up to 40 cm, with the internodes between basal foliage and first leaflet length being 6 cm and the second internodes between the first leaflet and the second leaflet length being 9 cm and the third internodes between the second and third leaflet length being 8 cm.

*Stem coloration.*—146 D at the base and blending into 187 B at the tip.

Foliage description:

*Type.*—Herbaceaous.

*Arrangement.*—Basal alternate with typically two or three lateral leaflets per stem.

*Petiole.*—Up to 19 cm long, with a diameter of 2 mm, color is 187 B.

*Terminal compound leaf length.*—Up to 5 cm.

*Terminal compound leaf width.*—3 cm.

*Terminal leaflet length.*—Typically 16 mm.

*Terminal leaflet width.*—Typically 10 mm.

*Terminal leaflet shape.*—Obovate with incised margins.

*Terminal and lateral leaf apex.*—Acute.

*Terminal and lateral leaf base.*—Cuneate.

*Terminal and lateral leaf margin.*—Incised.

*Texture.*—Terminal and lateral leaf, upper and lower surfaces: pubscent.

*Venation pattern.*—Terminal and lateral leaf, upper and lower surfaces: pinnate.

*Venation color.*—Terminal and lateral leaf, upper surface is color 138 A and lower surface color is 146 C.

*Lateral leaflet number.*—2 or 3 per stem.

*Lateral leaflet length.*—8 cm.

*Lateral leaflet width.*—Up to 4 cm.

*Lateral Leaflet shape.*—Obovate.

*Terminal and lateral adaxial leaf color description.*—138 A.

*Terminal and lateral abaxial leaf color description.*—146 C.

Flower description:

*Flower type.*—Corymb.

*Adaxial flower color.*—Pink RHS 185 C and 185 D fading to 159 A at the tips of the petals. Abaxial Flower color — 59 D.

*Flower size.*—Diameter: 40 mm across, depth 15 mm.

*Flower number.*—5 per stem, 50 per plant. Average Number Flowering Stems — 10.

*Bloom period and duration.*—Beginning the first week of May into the last week of May in Hebron, Ill.

*Flower longevity and duration on the plant.*—Approximately 2-3 weeks.

*Flower longevity and duration cut.*—Approximately 5 days.

*Scent.*—None.

*Petal count.*—From 5 up to 20.

*Petal arrangement.*—Rotate, overlapping.

*Petal diameter or width.*—18 mm across and petal length — 12 mm long.

*Petal apex.*—Retuse and lobulate, base: attenuate, margin: entire and sinuate.

*Petal texture.*—Upper and lower surfaces: smooth, glabrous.

*Petal color.*—Upper surface is pink 185 C and 185 D fading to 159 A at the tips of the petals.

*Petal color.*—Lower surface color is 59 D.

*Petal Venation.*—Type — reniform, vein color — upper surface 185 B, lower surface close to 185 B.

*Inflorescence diameter and height.*—8 cm across, 18 cm long.

*Flower buds.*—Diameter: 8 mm across, depth: 10 mm, shape: ovoid, surface: slightly pubescent and color 187 B.

*Sepal size.*—Length: up to 12 mm, diameter: 4 mm at base coming to a point.

*Sepal quantity.*—6.

*Sepal shape.*—Lanceolate, apex: acute, base: cuneate, margin: entire.

*Sepal texture.*—Upper and lower surfaces: Pubescent.

*Sepal color.*—Adaxial color 197 B. Abaxial color 187 B.

*Peduncle color.*—146 B at the base, blending into 187 B.

*Peduncle size.*—Length: 23 cm, diameter: 3 mm.

*Pedicel size.*—Length: 19 cm, diameter: 1-2 mm and color 187 B.

*Reproductive organs.*—Stamen — quantity 100-200 if present but they are not always present, length 3 cm.

*Anther.*—Quantity: 150, length: 1 mm, diameter: close to 0.5 mm.

*Pollen.*—Present but not always on every flower, sometimes absent, color: 12 A.

*Stigma.*—None observed.

*Style.*—Number: 75, length: 1-2 mm. Pistil — number: 75, length: 1-2 mm.

*Ovaries.*—None observed.

*Fruit.*—A cluster of achenes with 1-2 mm styles. Color — brown.

*Hardiness.*—USDA zone 4-8.

Disease Resistance: Resistance to diseases common to *Geum* has not been observed on plants grown under nursery conditions.

I claim:

1. A new, distinct *Geum* plant as illustrated and described, characterized by ruffled semi double to single pink flowers.

* * * * *